(12) United States Patent
Cho et al.

(10) Patent No.: US 9,192,597 B2
(45) Date of Patent: Nov. 24, 2015

(54) COMPOSITION FOR INHIBITING VASCULAR AGING COMPRISING SYRINGARESINOL

(71) Applicant: AMOREPACIFIC CORPORATION, Seoul (KR)

(72) Inventors: Si Young Cho, Yongin-si (KR); Chan Woong Park, Yongin-si (KR); Dae Bang Seo, Yongin-si (KR); Wan Gi Kim, Yongin-si (KR); Sang Jun Lee, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 48 days.

(21) Appl. No.: 14/350,668

(22) PCT Filed: Oct. 25, 2012

(86) PCT No.: PCT/KR2012/008815
§ 371 (c)(1),
(2) Date: Apr. 9, 2014

(87) PCT Pub. No.: WO2013/062332
PCT Pub. Date: May 2, 2013

(65) Prior Publication Data
US 2014/0248381 A1      Sep. 4, 2014

(30) Foreign Application Priority Data
Oct. 27, 2011   (KR) .................. 10-2011-0110486

(51) Int. Cl.
| | | |
|---|---|---|
| A01N 65/00 | (2009.01) |
| A61K 31/34 | (2006.01) |
| A61K 36/00 | (2006.01) |
| A23L 1/30 | (2006.01) |
| A61K 36/258 | (2006.01) |
| A61K 9/00 | (2006.01) |
| A61K 9/16 | (2006.01) |
| A61K 9/20 | (2006.01) |
| A61K 36/185 | (2006.01) |
| A61K 36/254 | (2006.01) |
| A61K 36/55 | (2006.01) |
| A61K 36/756 | (2006.01) |

(52) U.S. Cl.
CPC .............. *A61K 31/34* (2013.01); *A23L 1/3002* (2013.01); *A61K 9/0014* (2013.01); *A61K 9/0053* (2013.01); *A61K 9/0095* (2013.01); *A61K 9/1652* (2013.01); *A61K 9/2059* (2013.01); *A61K 36/00* (2013.01); *A61K 36/185* (2013.01); *A61K 36/254* (2013.01); *A61K 36/258* (2013.01); *A61K 36/55* (2013.01); *A61K 36/756* (2013.01); *A23V 2002/00* (2013.01)

(58) Field of Classification Search
CPC ....................................... A61K 36/00
USPC ........................................... 424/725
See application file for complete search history.

(56) References Cited

FOREIGN PATENT DOCUMENTS

| EP | 0519673 A1 | 12/1992 |
| EP | 0729753 A1 | 9/1996 |
| KR | 10-2004-0050396 | 6/2004 |

OTHER PUBLICATIONS

Jung et al., "In vivo Anti-Inflammatory and Antinociceptive Effects of Linodendrin Isolated from the Stem Bark of *Acanthopanax senticosus*," Planta Med. 69:610-16 (2003).
International Search Report for International Patent Application No. PCT/KR2012/008815 (mailed Mar. 26, 2013).

*Primary Examiner* — Michael Meller
(74) *Attorney, Agent, or Firm* — Merchant & Gould P.C.

(57) ABSTRACT

The present invention discloses a composition for inhibiting vascular aging comprising a compound of Chemical formula 1, a derivative thereof or a pharmaceutically acceptable salt thereof as an active ingredient.

4 Claims, 5 Drawing Sheets

COMPOSITION FOR INHIBITING VASCULAR AGING COMPRISING SYRINGARESINOL

This application is a U.S. National Stage Application under 35 U.S.C. §371 of International Patent Application No. PCT/KR2012/008815, filed 25 Oct. 2012, which claims the benefit of priority to Korean Patent Application No. 10-2011-0110486, filed 27 Oct. 2011, the disclosures of all of which are hereby incorporated by reference in their entireties. The International Application was published in Korean on May 2, 2013 as WO 2013/062332.

TECHNICAL FIELD

The present disclosure relates to composition for inhibiting vascular aging containing a compound of Chemical Formula 1, a derivative thereof or a pharmaceutically acceptable salt thereof as an active ingredient.

BACKGROUND ART

Vascular endothelial cells can constrict and/or dilate blood vessels by releasing endothelium-derived nitric oxide (NO) and prostanoids and activating or degrading hormones related with vascular activity and thereby regulating the function of vascular smooth muscle.

As vascular endothelial cells age, their telomerase activity decreases. Also, aged vascular endothelial cells exhibit significantly decreased vasoconstiriction ability due to decreased NO production, endothelial nitric oxide synthase (eNOS) expression and prostacyclin production, facilitated thrombosis due to increased plasminogen activator type 1 (PAI-1) expression, and narrowing of blood vessels due to increased expression of cell adhesion molecules and chemokines such as intercellular adhesion molecule 1 (ICAM-1), interleukin-1 and interleukin-8 and increased inflammatory responses. Indeed, it is known that the vascular endothelial cells of arteriosclerotic tissues exhibit increased activity of senescence-associated beta-galactosidase (SA-β-gal), which is well known as a cellular aging marker, as compared to the cells of normal tissues. In addition, the cells of the arteriosclerotic tissues show shorter telomere length as compared to the cells of normal tissues.

Accordingly, it will be possible to prevent and treat cardiovascular diseases by preventing or postponing the aging of vascular endothelial cells. The best known method for delaying vascular aging is to restrict calorie intake. However, since this method is practically difficult to adopt and causes inconvenience in daily lives, an alternative method is necessary.

DISCLOSURE

Technical Problem

The present disclosure is directed to providing a composition exhibiting superior effect of preventing vascular aging by increasing SIRT1 expression and activating telomerase in vascular cells and also exhibiting superior effect of preventing or improving cardiovascular diseases. The present disclosure is also directed to providing a food composition and a pharmaceutical composition exhibiting excellent effect of preventing vascular aging.

Technical Solution

In an aspect, the present disclosure provides composition for inhibiting vascular aging containing a compound of Chemical Formula 1, a derivative thereof or a pharmaceutically acceptable salt thereof as an active ingredient.

Advantageous Effects

A composition according to the present disclosure, which contains a compound of Chemical Formula 1, specifically syringaresinol, as an active ingredient may exhibit excellent effect of preventing vascular aging and, in particular, preventing or improving cardiovascular diseases by promoting SIRT1 expression in vascular cells, activating telomerase and allowing smooth constriction/dilation of blood vessels.

BEST MODE FOR CARRYING OUT INVENTION

Figure 1:
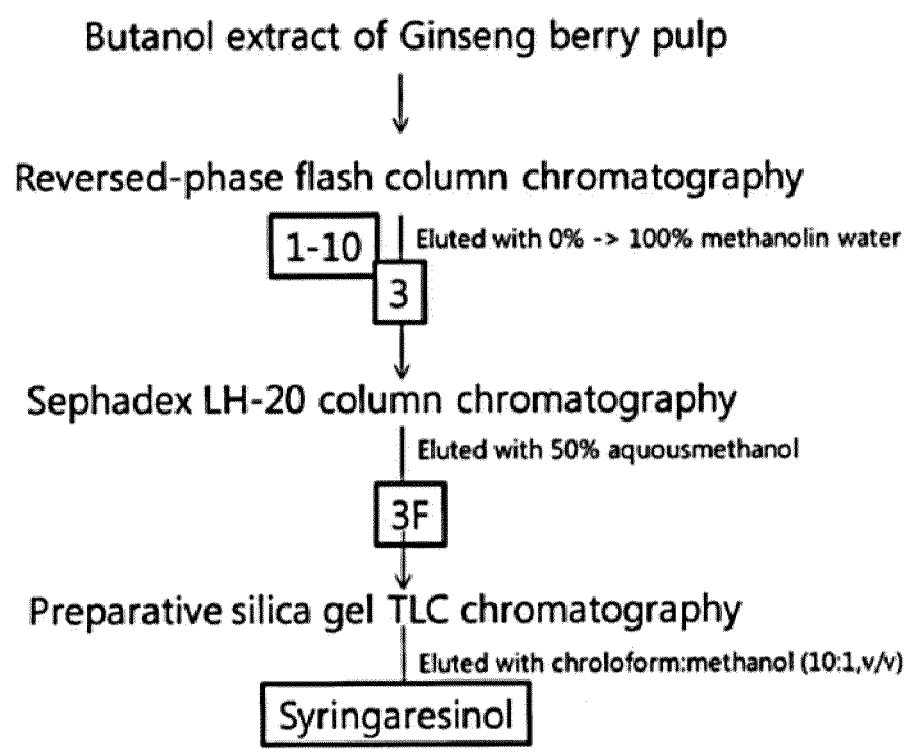
FIG. 1 schematically describes a method of isolating and purifying syringaresinol from a ginseng berry extract.

In the present disclosure, the term "extract" is used as a broad concept and refers to any substance extracted from a natural product, regardless of extraction method, extraction solvent, extracted ingredients or the type of extract.

As used herein, the term "derivative" refers to any compound having substituent(s) at substitutable position(s) of the corresponding compound. The substituent is not particularly limited. For example, the substituent may independently be a $C_{1-10}$ acyclic hydrocarbon group which may be substituted with hydroxyl, phenoxy, thienyl, furyl, pyridyl, cyclohexyl, alkylalcohol, alkyldialcohol or substituted phenyl; a $C_{5-6}$ cyclic hydrocarbon group which may be substituted with hydroxyl, hydroxymethyl, methyl or amino; or a sugar residue, although not being limited thereto. As used herein, the term "sugar residue" refers to the group available on elimination of one hydrogen atom from a carbohydrate molecule. As such, it may mean, for example, a residue derived from a monosaccharide or an oligosaccharide.

As used herein, the term "pharmaceutically acceptable" means being devoid of substantial toxic effects when used with a usual medicinal dosage and thereby being approvable or approved by a regulatory agency of the government or being listed in the US Pharmacopoeia or other generally recognized pharmacopoeia for use in animals, more particularly in human.

As used herein, the term "pharmaceutically acceptable salt" refers to a salt of the compound of the present disclosure which is pharmaceutically acceptable and possesses the desired pharmacological activity of the parent compound. The salt may include: (1) an acid addition salt formed with an inorganic acid such as hydrochloric acid, hydrobromic acid, sulfuric acid, nitric acid, phosphoric acid, etc. or formed with an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, ethane-1,2-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is replaced. In addition to the pharmaceutically acceptable salt, the compound according to the present disclosure may include any salt, hydrate or solvate that can be prepared according to commonly employed methods.

Hereinafter, the present disclosure is described in detail.

It is known that restriction of calorie intake leads to increased SIRT1 expression in vascular endothelial cells. Sirtuin 1 (SIRT1) is an $NAD^+$-dependent histone deacetylase which regulates various processes including energy metabolism, hormone signaling, stress response, etc. Accordingly, a substance which promotes the expression of SIRT1 in vascular cells is expected to be capable of preventing and treating cardiovascular diseases including arteriosclerosis by preventing the aging of vascular endothelial cells as in the case of calorie intake restriction.

In an aspect, the present disclosure provides a composition for inhibiting vascular aging containing a compound of Chemical Formula 1, a derivative thereof or a pharmaceutically acceptable salt thereof as an active ingredient:

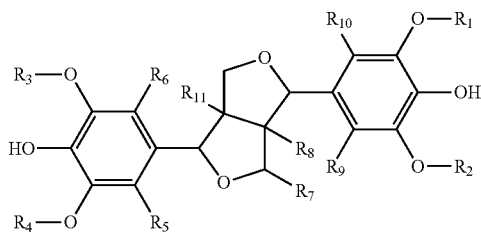

(Chemical Formula 1)

wherein $R_1$, $R_2$, $R_3$ or $R_4$ is independently an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group, and $R_5$, $R_6$, $R_7$, $R_8$, $R_9$, $R_{10}$ or $R_{11}$ is independently hydrogen or an unbranched or branched, $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group.

In an exemplary embodiment of the present disclosure, the compound may be syringaresinol.

As used herein, the term "syringaresinol" refers to a lignan-based compound having a chemical structure represented by Chemical Formula 2. It may be synthesized chemically or extracted from one or more of flax seed, phellodendri cortex, acanthopanacis cortex, sesame seed and ginseng berry. The flax seed, phellodendri cortex, acanthopanacis cortex and sesame seed respectively include all parts of the plant, for example, leaves, stem, root, fruit or seed and the ginseng berry includes the rind or pulp of ginseng berry.

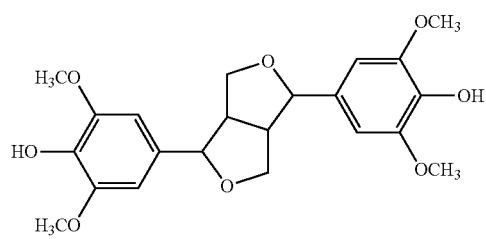

(Chemical Formula 2)

In the present disclosure, the "syringaresinol" may be obtained by extracting one or more of flax seed, phellodendri cortex, acanthopanacis cortex, sesame seed and ginseng berry with water, an organic solvent or a mixture of water and an organic solvent. The organic solvent includes one or more selected from a group consisting of alcohol, acetone, ether, ethyl acetate, diethyl ether, methyl ethyl ketone and chloroform, although not being limited thereto. The alcohol includes a $C_1$-$C_5$ lower alcohol and the $C_1$-$C_5$ lower alcohol includes one or more selected from a group consisting of methanol, ethanol, isopropyl alcohol, n-propyl alcohol, n-butanol and isobutanol, although not being limited thereto.

In an exemplary embodiment of the present disclosure, syringaresinol may be isolated and purified from ginseng berry by a procedure including: preparing an alcohol extract of ginseng berry pulp; eluting the prepared alcohol extract with a solvent including one or more of water and alcohol and obtaining fractions thereof; and performing chromatography, specifically thin-layer chromatography (TLC), on the obtained fractions using an organic solvent as an eluent. The organic solvent may include one or more selected from a group consisting of alcohol, acetone, ether, ethyl acetate, diethyl ether, methyl ethyl ketone and chloroform, and the alcohol may include a $C_1$-$C_5$ alcohol. In an exemplary embodiment of the present disclosure, the composition may contain the syringaresinol purified as described above as an active ingredient.

The compound of Chemical Formula 1, specifically syringaresinol, may promote the SIRT1 expression and telomerase activation and decrease the activity of the aging marker SA-β-gal in vascular endothelial cells and, thereby, may prevent the aging of vascular cells. Aged cells exhibit decreased vasoconstirction/vasodilation ability due to decreased NO production and decreased eNOS expression, and facilitated thrombosis due to increased PAI-1 expression. The compound of Chemical Formula 1, specifically syringaresinol, may prevent the aging of vascular cells and restore the function of aged vascular cells by increasing eNOS expression and, at the same time, decreasing PAI-1 expression. Accordingly, a composition containing the compound of Chemical Formula 1, specifically syringaresinol, as an active ingredient may prevent vascular aging.

Cardiovascular diseases are diseases related with disorder of blood supply to tissues as a result of blockage of blood vessels or leakage of blood outside the vessel walls and representative examples include cerebral infarction, cerebral hemorrhage, ischemic heart disease, myocardial infarction, arteriosclerosis, etc. The cardiovascular diseases may occur as vascular endothelial cells age and functional abnormalities are accumulated as a result thereof. Since the composition according to the present disclosure, which contains syringaresinol as an active ingredient, has superior effect of preventing vascular aging, it may exhibit excellent effect of preventing or improving cardiovascular diseases, especially aging-related cardiovascular diseases.

In another exemplary embodiment of the present disclosure, the syringaresinol may be contained in the composition as an extract of flax seed, phellodendri cortex, acanthopanacis cortex, sesame seed or ginseng berry. Specifically, it may be contained in a fraction which is particularly effective for preventing vascular aging.

In an exemplary embodiment of the present disclosure, the composition may contain the active ingredient in an amount of 1-80 wt %, specifically 5-60 wt %, more specifically 10-30 wt %, based on the total weight of the composition. This range is appropriate not only to derive the effect desired by the present disclosure and satisfy both the stability and safety of the composition but also in terms of cost effectiveness. Specifically, if the content of the syringaresinol is less than 1 wt %, sufficient vascular aging preventing effect may not be achieved. And, if it exceeds 80 wt %, the safety and stability of the composition may be unsatisfactory.

In another aspect, the present disclosure provides food composition containing syringaresinol as an active ingredient. The food composition may prevent vascular aging and, furthermore, may prevent or improve cardiovascular diseases such as cerebral infarction, cerebral hemorrhage, ischemic heart disease, myocardial infarction or arteriosclerosis. In an exemplary embodiment of the present disclosure, the food composition may include an indulgence food or health food composition.

The formulation of the food composition is not particularly limited. For example, it may be formulated into tablet, granule, powder, liquid such as drink, caramel, gel, bar, etc. Those skilled in the art may select and add the ingredients commonly used in the art to each formulation of the food composition without difficulty. In this case, a synergic effect may be achieved.

Determination of the dosage of the active ingredient is in the level of those skilled in the art. A daily dosage may be, for example, 0.1-5000 mg/kg/day, more specifically 50-500 mg/kg/day. However, the dosage may vary depending on various factors including the age and physical condition of a subject, the presence or absence of complication(s), or the like, without being limited thereto.

In another aspect, the present disclosure provides a pharmaceutical composition containing syringaresinol as an active ingredient. The pharmaceutical composition may prevent vascular aging and, in particular, may prevent or treat cardiovascular diseases such as cerebral infarction, cerebral hemorrhage, ischemic heart disease, myocardial infarction or arteriosclerosis.

In an exemplary embodiment of the present disclosure, the pharmaceutical composition may be administered orally or parenterally, e.g., rectally, topically, transdermally, intravenously, intramuscularly, intraperitoneally, subcutaneously, etc.

A formulation for oral administration may be tablet, pill, soft or hard capsule, granule, powder, fine granule, liquid, emulsion or pellet, although not being limited thereto. These formulations may further contain, in addition to the active ingredient, a diluent (e.g., lactose, dextrose, sucrose, mannitol, sorbitol, cellulose or glycine), a lubricant (e.g., silica, talc, stearic acid or polyethylene glycol) or a binder (e.g., magnesium aluminum silicate, starch paste, gelatin, tragacanth, methyl cellulose, sodium carboxymethyl cellulose or polyvinylpyrrolidone). In some cases, they may further contain a pharmaceutical additive such as a disintegrant, an absorbent, a colorant, a flavoring agent, a sweetener, etc. The tablet may be prepared according to the common mixing, granulation or coating method.

A formulation for parenteral administration may be collyrium, injection, drop, lotion, ointment, gel, cream, suspension, emulsion, suppository, patch or spray, although not being limited thereto.

The dosage of the active ingredient of the pharmaceutical composition according to the present disclosure will vary depending on the age, sex and body weight of a subject, particular pathological condition and severity thereof, administration route or the discretion of a diagnoser. Determination of the dosage considering these factors is in the level of those skilled in the art. A daily dosage may be, for example, 0.1-100 mg/kg/day, more specifically 5-50 mg/kg/day, although not being limited thereto.

Mode for Invention

Hereinafter, the present disclosure will be described in detail through an example and test examples. However, the following example and test examples are for illustrative purposes only and it will be apparent to those of ordinary skill in the art that the scope of the present disclosure is not limited by the example and test examples.

EXAMPLE

Isolation and Analysis of Syringaresinol

1. Pretreatment of Ginseng Berry

Live ginseng berry was harvested. After removing the seed and rind of the ginseng berry, only the pulp was dried under sunlight or using hot air to obtain dried ginseng berry pulp.

2. Isolation of Syringaresinol from Ginseng Berry Pulp Extract and Analysis Thereof 3. L of water or alcohol was added to 1 kg of the dried ginseng berry pulp. After extracting at room temperature or under reflux, followed by filtering and concentration at 40-45° C. under reduced pressure, 300 g of a ginseng berry pulp extract was obtained. The extract was treated with ether to remove oil-soluble components and then crude saponin was extracted with butanol and concentrated. Then, syringaresinol was isolated and purified therefrom as follows. First, 194 g of the sample was purified by reversed-phase (ODS) column chromatography. As the eluent, 100% water was used in the beginning. Subsequently, methanol was increased gradually by 10% and, finally, 100% methanol was used as the eluent. As a result, fractions GB-1 through GB-10 were obtained. Among the fractions, the fraction GB-3 which exhibits sirtuin 1 (SIRT1) expression activity was concentrated and subjected to Sephadex LH-20 column chromatography using 50% aqueous methanol. Among the resulting fractions, the fraction GB-3-6(3F) exhibiting SIRT1 expression activity was concentrated and subjected to preparative silica gel TLC using chloroform:methanol (10:1) as an eluent. As a result, an active fraction with an $R_f$ value of 0.67 was purified. This procedure is schematically described in FIG. 1.

Through NMR spectroscopic analysis and database search, the isolated and purified active compound was identified as syringaresinol. Mass analysis was conducted to confirm this. As a result of ESI-mass analysis in the positive mode, $[M+Na]^+$ (m/z=440.9) and $[2M+Na]^+$ (m/z=858.9) peaks were observed and the molecular weight was calculated as 418. And, the result of NMR spectroscopic analysis was as in Chemical Formula 3. Accordingly, the isolated and purified active compound was confirmed to be syringaresinol.

(Chemical Formula 3)

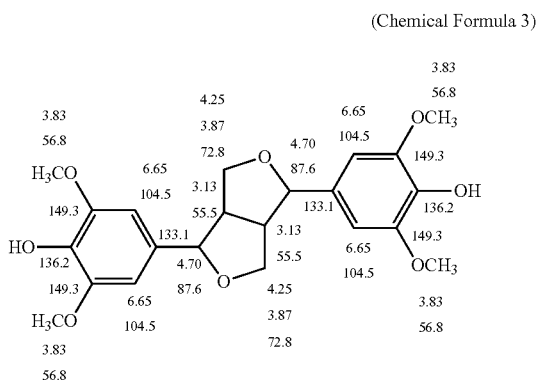 [SMILES: COc1cc(C2OCC3C(c4cc(OC)c(O)c(OC)c4)OCC23)cc(OC)c1O]

As such, syringaresinol was isolated from the ginseng berry pulp.

Test Example 1

Evaluation of SIRT1 Expression Promoting Effect in Aged Human Vascular Endothelial Cells The SIRT1 gene expression promoting effect of syringaresinol in aged human vascular endothelial cells was evaluated as follows.

Human vascular endothelial cells purchased from Lonza (Walkersville, Md., USA) were cultured using the endothelial cell growth medium EGM-2 SingleQuots (Lonza) in a 5% $CO_2$ incubator until 70% confluency. The aging of the vascular endothelial cells was induced by subculturing until they did not grow any more. The population doubling level (PDL) was calculated according to the following equation for each generation until the cell growth was stopped. The PDL value is higher in aged cells.

$PDL=(Log_{10} Y - Log_{10} X)/Log_{10} 2$

Y: number of cells at the end of the generation
X: number of cells at the beginning of the generation 14 PDL cells were treated with syringaresinol dissolved in DMSO at a concentration of 20, 50 or 100 μM every other day while inducing aging to 40 PDL cells. The cells of a negative control group were treated with DMSO of 1/1000 of the volume of the medium. The cells treated with each sample were washed 2 times with cold PBS and RNA was extracted using TRIzol reagent (Invitrogen). cDNA was synthesized from the extracted RNA (1 μg/μL) using a reverse transcription system (Promega). Subsequently, the expression pattern of the SIRT1 and GAPDH genes was measured using the synthesized cDNA and predesigned primers and probes (Applied Biosystems; SIRT1, Hs01009006_m1; GAPDH, Hs99999905_m1). PCR reaction and analysis were carried out using the Rotor-Gene 3000 system (Corbett Research, Sydney, Australia). The result is shown in FIG. 2.

Figure 2:
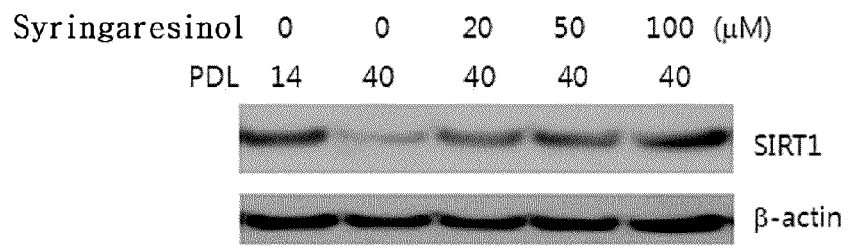
FIG. 2 shows that the expression of the SIRT1 gene is increased in aged vascular cells treated with syringaresinol.

As seen from FIG. 2, syringaresinol increases the decreased SIRT1 expression in aged vascular endothelial cells in a concentration-dependent manner. Accordingly, it can be seen that syringaresinol can prevent vascular aging and, furthermore, can prevent or improve cardiovascular diseases.

Test Example 2

Evaluation of Aging Marker Inhibiting Effect in Aged Vascular Endothelial Cells

Figure 3:
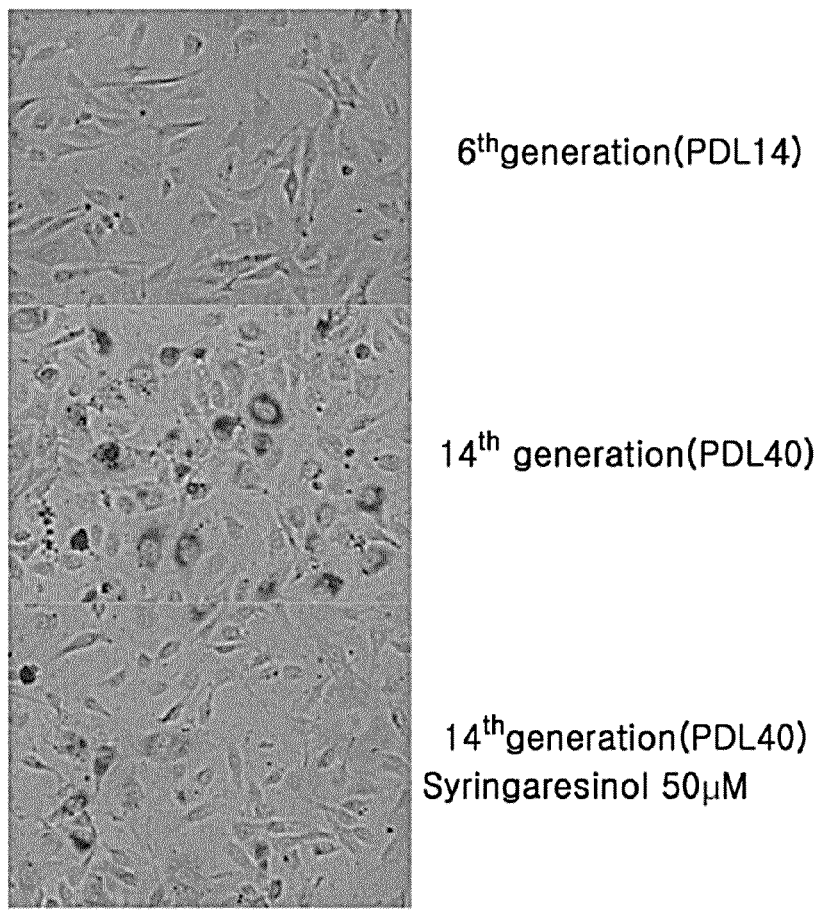
FIG. 3 shows images showing the level of an aging marker in aged vascular cells treated with syringaresinol.

The aging of vascular endothelial cells was induced by treating with 50 μM syringaresinol in substantially the same manner as in Test Example 1. The aged cells were washed with PBS and stained at 37° C. for 16 hours using a fixative and a stain provided together with the Cellular Senescence Assay kit (Cell Biolabs, Inc., San Diego, Calif., USA). Next day, the cells were washed with PBS, overlaid with 20% glycerol solution and observed under a microscope. The result is shown in FIG. 3. The number of the cells stained green was counted and the activity of the aging marker SA-β-gal was determined. The result is shown in FIG. 4.

Figure 4:
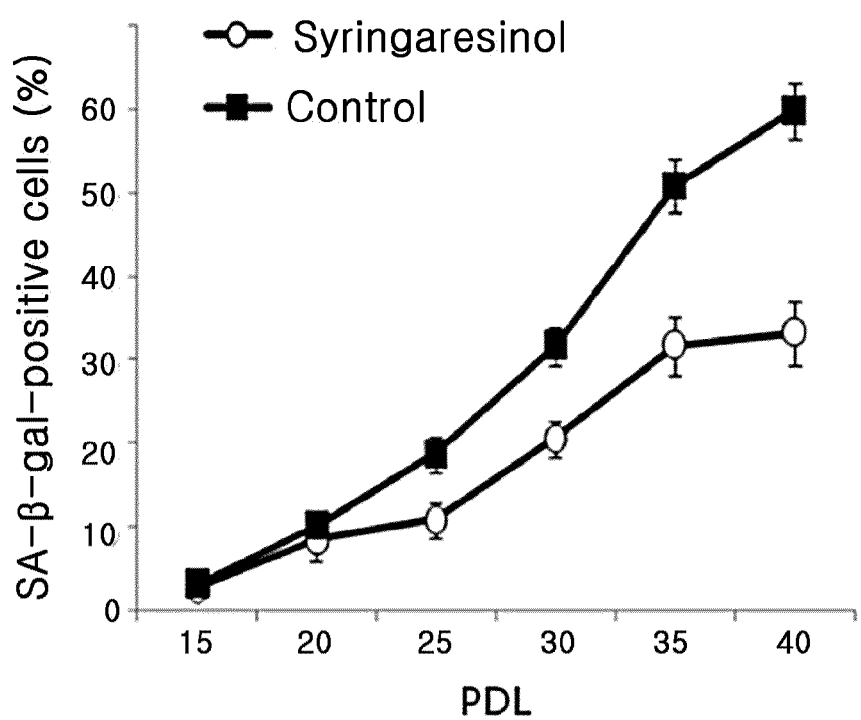
FIG. 4 shows the amount of an aging marker in aged vascular cells treated with syringaresinol.

As seen from FIG. 3 and FIG. 4, the cells treated with syringaresinol show a remarkably smaller number of green-stained cells as compared to the cells treated only with DMSO and exhibit approximately as much as 50% deceased SA-β-gal activity. Accordingly, it can be seen that syringaresinol can prevent or improve cardiovascular diseases by preventing vascular aging.

Test Example 3

Evaluation of Telomerase Activity Enhancing Effect in Aged Vascular Endothelial Cells The aging of vascular endothelial cells was induced by treating with 50 μM syringaresinol or DMSO as control in substantially the same manner as in Test Example 1. The aged cells were washed with PBS and lysed using lysis buffer (Sigma), and the obtained protein was quantitated. Telomerase activity was evaluated using the TeloTAGGG telomerase PCR ELISA Plus kit (Roche Applied Science, Indianapolis, Ind., USA). The result is shown in FIG. 5.

Figure 5:
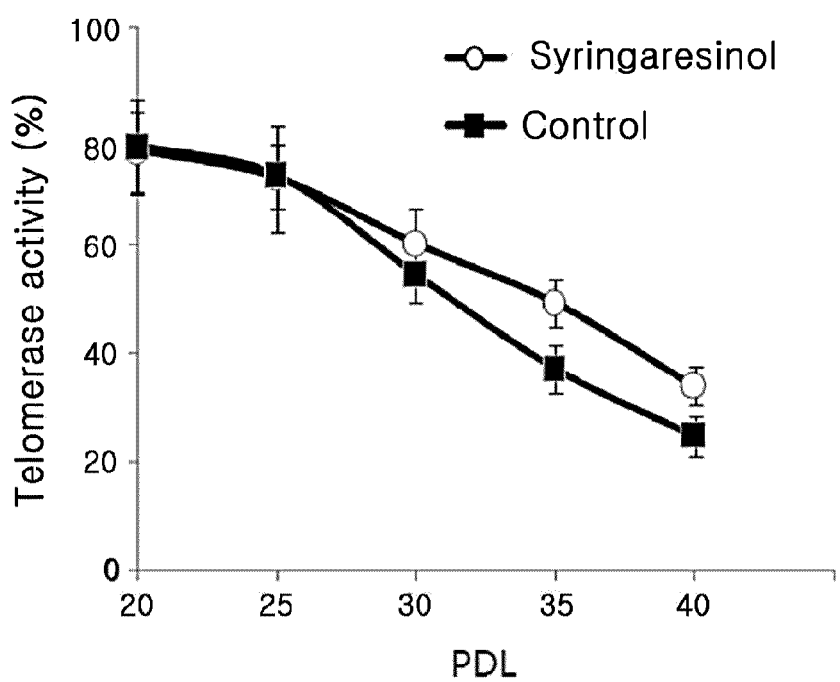
FIG. 5 shows the activity of telomerase in aged vascular cells treated with syringaresinol.

As seen from FIG. 5, the cells treated with syringaresinol show about 30% increased telomerase activity as compared to the cells treated only with DMSO. Accordingly, it can be seen that syringaresinol can prevent vascular aging and prevent or improve cardiovascular diseases by activating telomerase in aged vascular cells.

Test Example 4

Evaluation of Restoring Function of Aged Vascular Endothelial Cells

In order to evaluate whether syringaresinol can restore the declined function of aged vascular cells to that of young vascular cells, the aging of vascular endothelial cells was induced by treating with 50 μM syringaresinol or DMSO as control in substantially the same manner as in Test Example 1. Aged cells exhibit decreased vasoconstiriction/vasodilation ability due to decreased NO production and decreased eNOS expression, and facilitated thrombosis due to increased PAI-1 expression. As a result, cardiovascular diseases such as arteriosclerosis can occur easily. The cells treated with syringaresinol or DMSO were washed with PBS and lysed with lysis buffer (Sigma), and the supernatant was recovered. Then, protein present in the supernatant was quantitated using Protein Dye Reagent™ (Bio-Rad). 100 μg of the obtained protein was fractionated by size by electrophoresing on 8% SDS-PAGE and transferred onto PVDF membrane (Bio-Rad) for 12 hours with 50 V. Then, the membrane was blocked for 1 hour with 5% non-fat milk and treated with anti-eNOS, anti-PAI-1 and anti-actin antibodies, as primary antibodies, and horse radish peroxidase (HRP)-conjugated anti-rabbit IgG (Amersham) as secondary antibody, and reacted using the enhanced chemiluminescence (ECL) kit (Amersham). The reacted PVDF membrane exposed to X-ray Fuji film and developed to investigate the protein expression level. The result is shown in FIG. 6.

Figure 6:
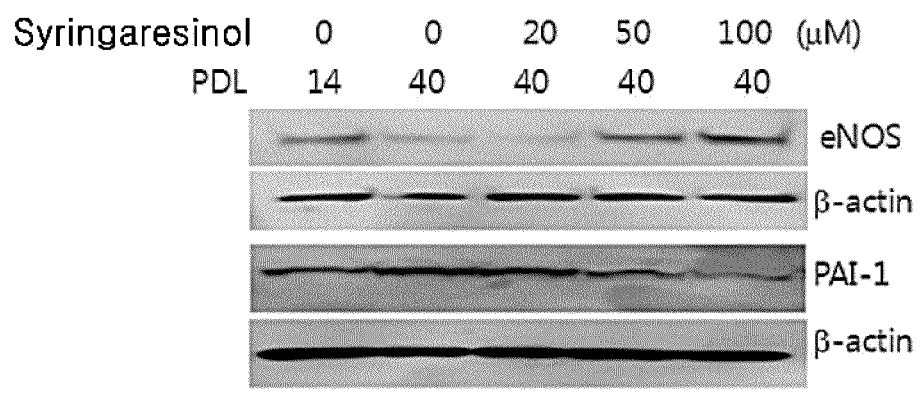
FIG. 6 shows the expression level of eNOS and PAI-1 in aged vascular cells treated with syringaresinol.

As seen from FIG. 6, the cells treated with syringaresinol show increased eNOS expression comparable to that of young cells and also show decreased PAI-1 expression comparable to that of young cells. Accordingly, it can be seen that syringaresinol can prevent vascular aging and prevent or improve cardiovascular diseases by restoring the vasoconstiriction/vasodilation function of aged vascular cells, thrombosis.

Hereinafter, the present disclosure will be described in detail through formulation examples. However, the formulation examples are for illustrative purposes only and it will be apparent to those of ordinary skill in the art that the scope of the present disclosure is not limited by the formulation examples.

Formulation Example 1

Health Food

| | |
|---|---|
| Syringaresinol | 1000 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium dihydrogen phosphate | 15 mg |
| Calcium monohydrogen phosphate | 55 mg |
| Potassium citrate | 90 mg |
| Calcium carbonate | 100 mg |
| Magnesium chloride | 24.8 mg |

Although the above-described mixing ratios of the vitamin and mineral mixtures are provided as specific examples suitable for health food, the mixing ratios may be changed as desired.

Formulation Example 2

Health Drink

| | |
|---|---|
| Syringaresinol | 1000 mg |
| Citric acid | 1000 mg |
| Oligosaccharide | 100 g |
| Taurine | 1 g |
| Purified water | balance |

According to a commonly employed method, the above-described ingredients are mixed and stirred for about 1 hour while heating at about 85° C. The resulting solution is filtered and sterilized.

Formulation Example 3

Tablet

Granules formed by mixing 100 mg of syringaresinol, 50 mg of soybean extract, 100 mg of glucose, 50 mg of red ginseng extract, 96 mg of starch and 4 mg of magnesium stearate and adding 40 mg of 30% ethanol are dried at 60° C. and prepared into a tablet.

Formulation Example 4

Granule

Granules formed by mixing 100 mg of syringaresinol, 50 mg of soybean extract, 100 mg of glucose and 600 mg of starch and adding 100 mg of ethanol are dried at 60° C. and filled in a pouch.

Formulation Example 5

Ointment

An ointment is prepared according to a commonly employed method with the following composition.

TABLE 1

| Ingredients | Content (wt %) |
|---|---|
| Syringaresinol | 3.0 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, pigment and fragrance | adequate |
| Purified water | balance |

INDUSTRIAL APPLICABILITY

A composition according to the present disclosure, which contains a compound of Chemical Formula 1, specifically syringaresinol, as an active ingredient, can prevent vascular aging by promoting SIRT1 expression, activating telomerase and restoring vasoconstiriction/vasodilation ability of vascular cells and, in particular, exhibits excellent effect of preventing or improving cardiovascular diseases.

We claim:

1. A method of treating a human suffering from a disease selected from the group consisting of cerebral infarction, cerebral hemorrhage, ischemic heart disease, myocardial infarction and arteriosclerosis comprising administering to the human a therapeutically effective amount of isolated syringaresinol to effectively treat the disease in the human.

2. The method according to claim 1, wherein the syringaresinol is administered in a form of a composition comprising 0.001-80 wt % of the syringaresinol based on the total weight of the composition.

3. The method according to claim 2, wherein the composition is a food composition.

4. The method according to claim 2, wherein the composition is a pharmaceutical composition.

* * * * *